(12) United States Patent
Laudermilch et al.

(10) Patent No.: US 10,265,729 B2
(45) Date of Patent: Apr. 23, 2019

(54) PHASED ARRAY ULTRASONIC TRANSDUCERS WITH SOLDERLESS STACK BONDING ASSEMBLY

(71) Applicants: James Laudermilch, Lewistown, PA (US); Terry Wray, McClure, PA (US)

(72) Inventors: James Laudermilch, Lewistown, PA (US); Terry Wray, McClure, PA (US)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 529 days.

(21) Appl. No.: 15/010,524

(22) Filed: Jan. 29, 2016

(65) Prior Publication Data

US 2016/0231289 A1    Aug. 11, 2016

Related U.S. Application Data

(60) Provisional application No. 62/112,933, filed on Feb. 6, 2015.

(51) Int. Cl.
*G01N 29/24* (2006.01)
*G01N 29/26* (2006.01)
*B06B 1/06* (2006.01)

(52) U.S. Cl.
CPC ............ *B06B 1/0622* (2013.01); *B06B 1/067* (2013.01); *G01N 29/245* (2013.01); *G01N 29/2437* (2013.01); *G01N 29/262* (2013.01); *G01N 2291/106* (2013.01)

(58) Field of Classification Search
CPC .. B06B 1/0622; B06B 1/067; G01N 29/2437; G01N 29/245; G01N 29/262

USPC .................................................. 310/322, 334
See application file for complete search history.

(56) References Cited

U.S. PATENT DOCUMENTS

| | | | | |
|---|---|---|---|---|
| 9,414,809 B2* | 8/2016 | Lee | ....................... | A61B 8/4281 |
| 2008/0178677 A1* | 7/2008 | Baumgartner | ........... | A61B 8/00 73/606 |
| 2011/0025172 A1* | 2/2011 | Harhen | ................. | B06B 1/0629 310/334 |
| 2011/0181149 A1* | 7/2011 | Shikata | ................. | B06B 1/0629 310/327 |
| 2013/0081470 A1* | 4/2013 | Kim | ................... | G01N 29/2437 73/632 |

(Continued)

FOREIGN PATENT DOCUMENTS

EP    2316343 A1 *  5/2011  ............... A61B 8/00
EP    3054293 A1 * 10/2016  ............. G01N 29/24

*Primary Examiner* — Thomas M Dougherty
(74) *Attorney, Agent, or Firm* — C. Tricia Liu

(57) ABSTRACT

Disclosed is an NDT/NDI probe array and manufacturing method. The probe array includes a sheet of flexible circuit 10 with a plurality of lower pins 102 and corresponding, electrically connected, upper pins 104. The probe further comprises a backing block 12, a layer of piezoelectric ceramic 16 having a plurality of conductive elements 162, a matching layer 18 and a frame 14. An adhesive material such as epoxy is applied to the circuit, the backing, the ceramic and the matching layer, and all are aligned and stack pressed at least partially into the frame and permanently bonded in such a fashion that each of the lower pins of the flexible circuit is firmly and permanently in contact with a corresponding one of the conductive elements of the ceramic.

20 Claims, 3 Drawing Sheets

(56) References Cited

U.S. PATENT DOCUMENTS

2013/0257226 A1\* 10/2013 Nobles ................. B06B 1/0622
 310/327
2014/0046188 A1\* 2/2014 Yen ..................... G10K 11/346
 600/444

\* cited by examiner

Section A-A

PHASED ARRAY ULTRASONIC TRANSDUCERS WITH SOLDERLESS STACK BONDING ASSEMBLY

CROSS REFERENCE TO RELATED APPLICATIONS

This application claims the benefit and priority of U.S. Provisional patent application Ser. No. 62/112,933 filed Feb. 6, 2015 entitled PHASED ARRAY ULTRASONIC TRANSDUCERS WITH SOLDERLESS STACK BONDING ASSEMBLY, the entire disclosure of which is incorporated herein by reference.

FIELD OF THE INVENTION

The present invention relates to non-destructive testing and inspection devices (NDT/NDI) and more particularly to manufacture of phased array ultrasonic testing (PAUT) transducers with a solderless stack bonding assembly method.

BACKGROUND OF THE INVENTION

PAUT transducers typically comprise a piezoelectric ceramic transducer array, with conductive elements deposited on the ceramic for making electrical contact with each transducer of the array, a backing material for acoustic damping and an electric circuit with pins for making contact with the conductive elements. The pins and electric circuit are often in the form of flexible printed circuit boards (PCBs). The conductive elements are formed from a thin film of conductive material, such as gold, which may be deposited by any suitable deposition method, such as sputtering, the film being patterned so that each conductive element is in electrical contact with one transducer of the array.

In existing practice, PAUT transducer assembly methods involve using soldering to attach the flexible circuit to the conductive elements. Soldering, even with a high level of automation, is typically time and labor consuming, which slows productivity.

In addition, soldering used in the PAUT industry for transducer manufacturing largely involves lead soldering. By 2017 the industry is required to be Restriction of Hazardous Substance (ROHS) compliant in order to ship product to the European Union. Consequently, lead free manufacturing will be required for this application.

Thus, there has been a need for an assembly process for making PAUT probes that can achieve precise, firm and permanent contacts between the PCB and the piezoelectric without using soldering.

SUMMARY OF THE INVENTION

The invention disclosed herein solves the problems related to existing assembly methods used for PAUT probe manufacturing that present the aforementioned drawbacks, such as low productivity and lead contamination. Note that the terms "probe", "transducer", and "sensor" used herein may be used interchangeably.

Accordingly, it is a general object of the present disclosure to provide a method and an NDT/NDI probe obtained by an assembly process that eliminates the need to solder.

It is further an object of the present disclosure to deploy a stack bond process which precisely aligns the pins of the PCB and the conductive elements on the piezoelectric ceramic.

It is further an object of the present disclosure to utilize a frame and pressure means to precisely, firmly and permanently achieve contacts between the pins of the PCB and the conductive elements on the piezoelectric ceramic.

It also can be understood that the presently disclosed probe provides the advantages of a shortened manufacturing cycle without any soldering.

BRIEF DESCRIPTION OF THE DRAWING(S)

DETAILED DESCRIPTION OF PREFERRED EMBODIMENT

Figure 1:
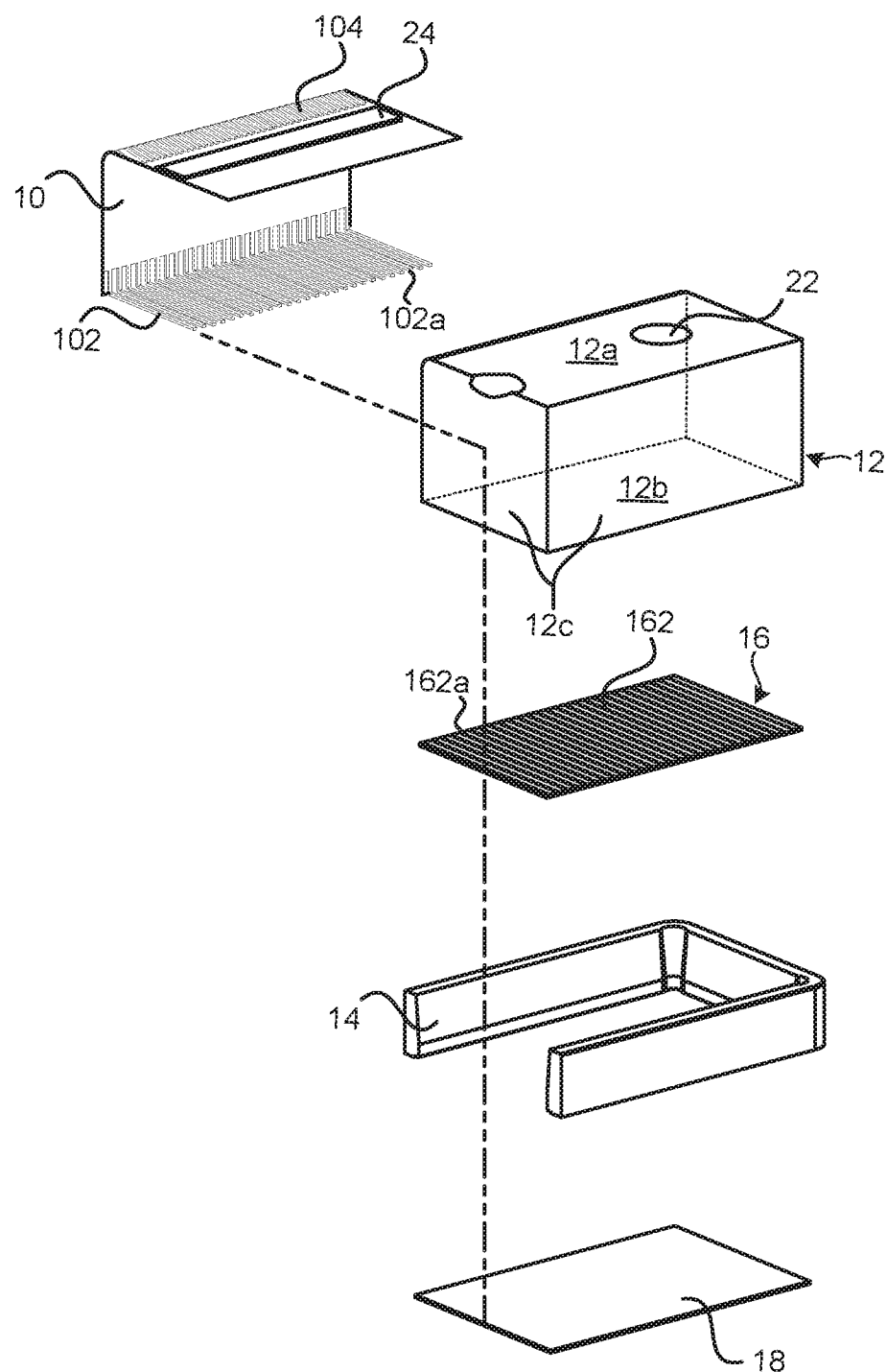
FIG. 1 is a half-section, exploded perspective view of a phased array ultrasonic transducer to be assembled according to the present disclosure.
Figure 2:
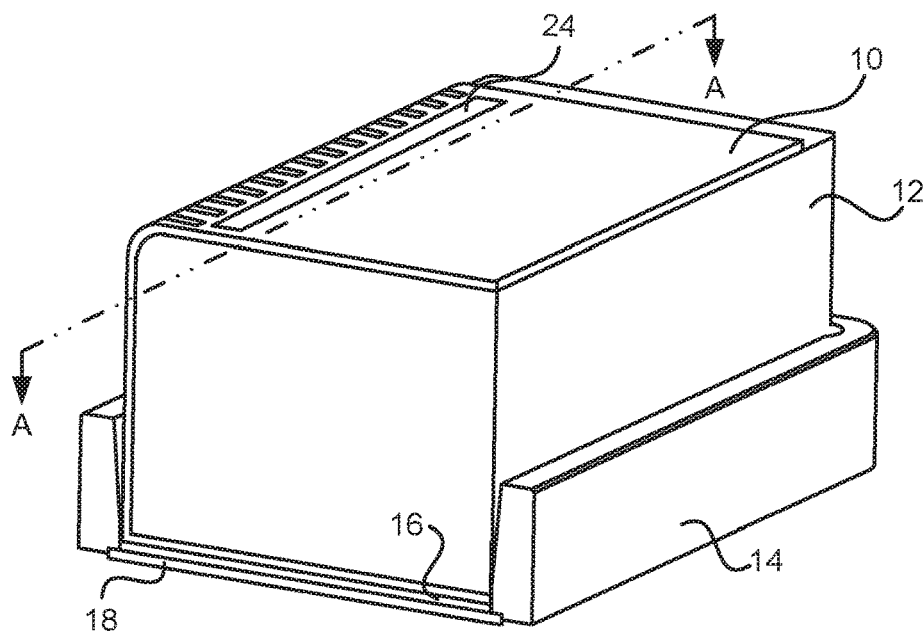
FIG. 2 is a half-section perspective view showing a flexible circuit sandwiched between the backing and the piezoelectric ceramic, where epoxy is applied to replace soldering.
Figure 3:
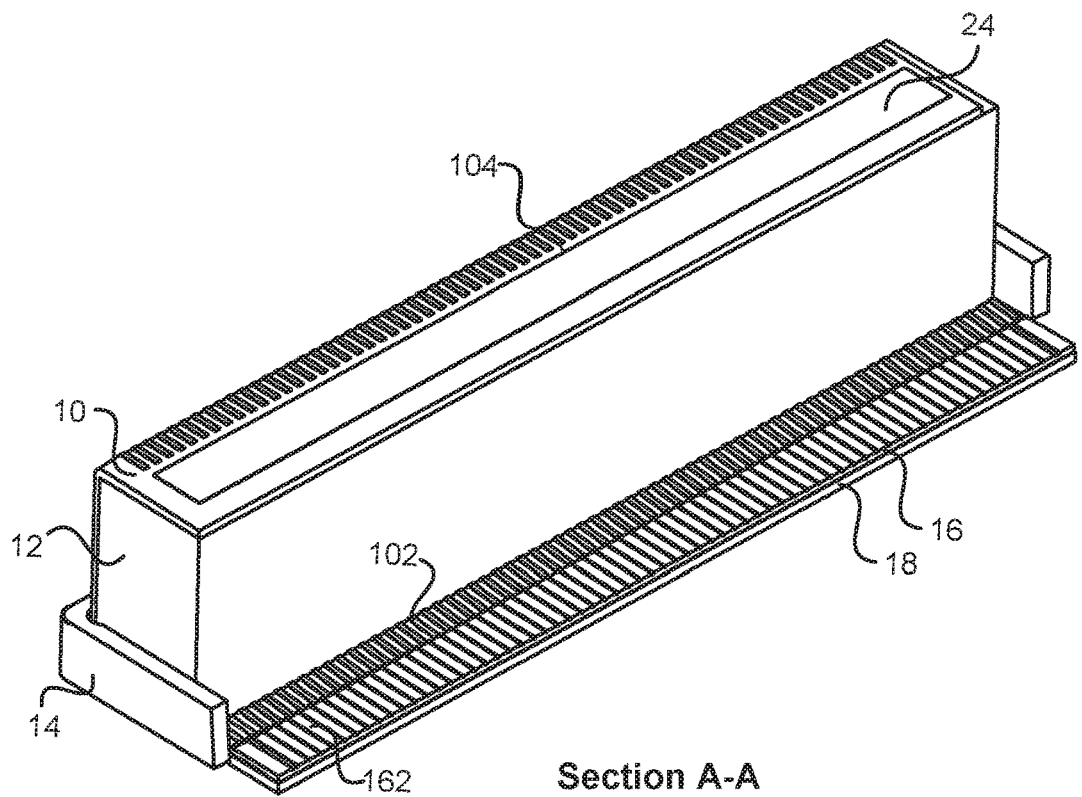
FIG. 3 is a perspective sectional view of a phased array ultrasonic transducer showing the pins of the flexible circuit matched with conductive elements on the piezoelectric ceramic according to the present disclosure.

FIG. 1 illustrates the assembly of a phased array ultrasonic transducer. As shown in FIGS. 1, 2 and 3, the PAUT probe comprises a flexible circuit 10, a frame 14, a piezoelectric ceramic 16, a matching layer 18, and a backing block 12, having a backing top 12a, a backing bottom 12b and backing sides 12c. Piezoelectric ceramic 16 comprises a plurality of transducers, with a plurality of conductive elements 162 close to a ceramic connecting edge 162a, for making electrical contact with each transducer. Flexible circuit 10 embodies a plurality of electrically conductive lower pins 102 at a flexible circuit connecting edge 102a, wherein each one of lower pins 102 is configured to make electrical contact with a corresponding one of conductive elements 162. Flexible circuit 10 also has a plurality of upper pins 104 whose purpose is to allow electrical contact to be made external to the phased array ultrasonic transducer. Each one of upper pins 104 is in electrical contact through flexible circuit 10 with a corresponding one of lower pins 102. A ground plane 24 is available on flexible circuit 10 in order to provide a common electrical ground connection for flexible circuit 10 and the transducers on piezoelectric ceramic 16.

It should be noted that conductive elements 162 are illustrated in FIGS. 1 and 3 as a one-dimensional array of lines, which would be appropriate for making contact with a one-dimensional array of transducers. However, in a further embodiment of the present invention, piezoelectric ceramic 16 may comprise a two-dimensional array of transducers, and conductive elements 162 are arranged in a corresponding two-dimensional array of conductive dots for making electrical contact with each transducer. In this embodiment, lower pins 102 would have different lengths, with the end of each pin being configured to make electrical contact with one of the conductive dots.

During assembly of the phased array ultrasonic transducer, lower pins 102 of flexible circuit 10 are required to form firm and permanent contacts to corresponding elements 162 of piezoelectric ceramic 16 in order to send electrical pulses to vibrate the ceramic and create ultrasonic sound waves. According to the present disclosure, such firm and permanent contacts are made by applying pressure and permanent bonding means. Frame 14, which may be made of any suitable electrically insulating material such as plastic, acts as an alignment tool for matching layer 18, piezoelectric ceramic 16, flexible circuit 10 and backing material 12. In addition, alignment holes 22 function to align pressure pins in a standard pressing tool (not shown), which may be activated by manual or other means to apply pressure between the layers in the ultrasonic transducer assembly. Note that frame 14 and backing block 12 have respective sizing and tolerance configured so that flexible circuit 10, backing block 12, piezoelectric ceramic 16 and matching layer 18 are all aligned and can be stack pressed at least partially into frame 14, below backing bottom 12b, and permanently bonded in such a fashion that each of the pins at flexible circuit connecting edge 102a is correspondingly, firmly and permanently in contact with a corresponding conductive element 162 at ceramic connecting edge 162a.

It should be noted that "edges" 102a and edge 162a do not have to be straight lines as shown in FIG. 1. They only represent the far ends of flexible circuit 10 and ceramic 16, respectively. In an alternative embodiment, "edges" 102a and edge 162a can take the form of uneven bars, with each pin of 102 and 162 having a different length, as long as the corresponding pins of 102 and 162 have endings or edges overlapped sufficiently, allowing them to be correspondingly, firmly and permanently in contact after being stack pressed. This alternative embodiment can be used for the situation wherein ceramic 16 comprises a two-dimensional array of transducers.

Referring to FIGS. 2 and 3, an adhesive such as epoxy is applied to permanently bond flexible circuit 10 in place and to maintain electrical connectivity between flexible circuit 10 and piezoelectric ceramic 16. Electrical connectivity between flexible circuit 10 and piezoelectric ceramic 16 is achieved by the stack bond process described in connection with FIG. 4 below.

FIG. 2 shows the stack consisting of matching layer 18, piezoelectric ceramic 16 and flexible circuit 10, all of which are compressed under pressure beneath backing block 12. Note that flexible circuit 10 is wrapped around backing block 12 on three sides. During compression, excess epoxy is squeezed out, particularly from between lower pins 102 and conductive elements 162, allowing good electrical contact to be made.

FIG. 3 is a section view along the line A-A shown in FIG. 2. FIG. 3 shows another view of the stack, with flexible circuit 10 and piezoelectric ceramic 16 sandwiched between backing block 12 and matching layer 18. In FIG. 3, backing block 12 and lower pins 102 have been cut back in order to show more clearly how lower pins 102 match up with conductive elements 162 of piezoelectric ceramic 16. Note that it is not necessary for pins 102 to extend all across the width of backing block 12 as shown in FIGS. 1 and 2. Shortening pins 102 as shown in FIG. 3 is acceptable, provided there is enough overlap between lower pins 102 and elements 162 to allow good electrical contact.

Figure 4:
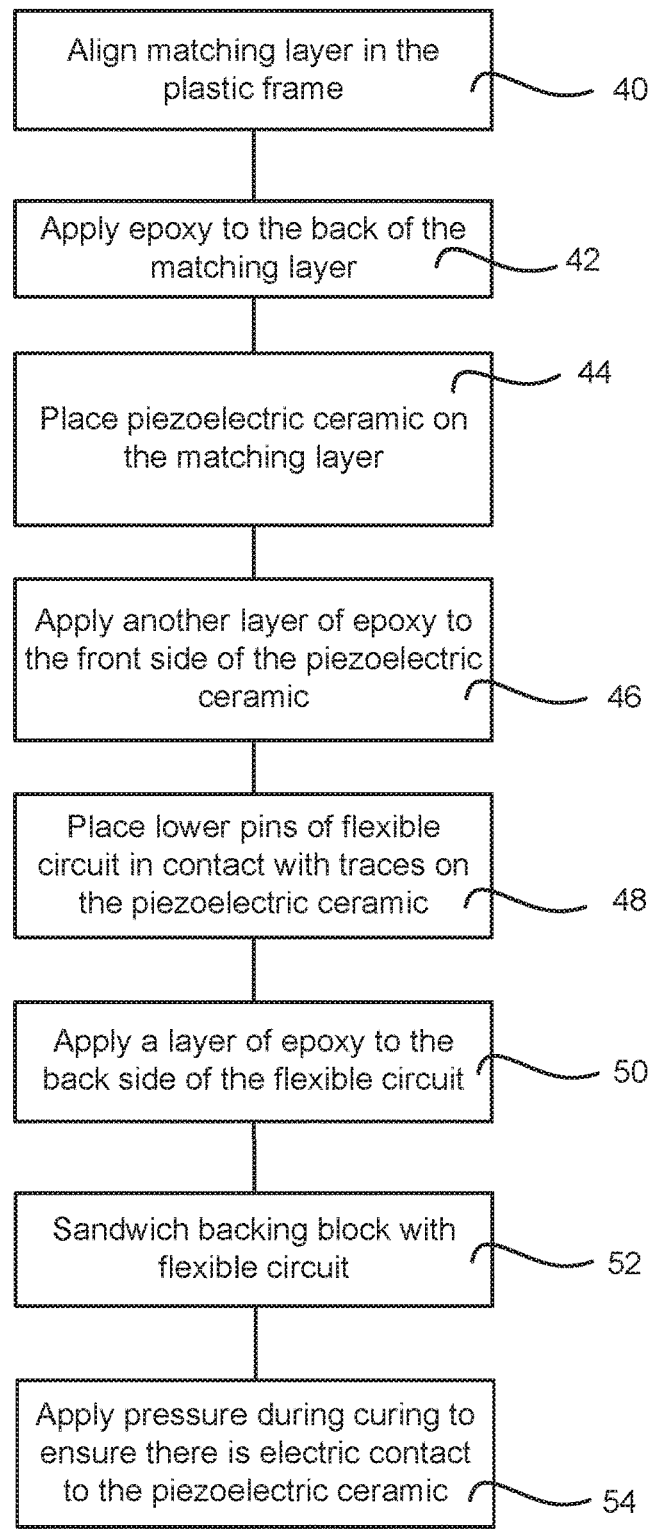
FIG. 4 is a flow chart showing the assembly process according to the present disclosure.

FIG. 4 shows the implementation steps of the solderless stack bond process. In step 40, matching layer 18 is aligned in frame 14. In step 42, an epoxy is applied to the back of matching layer 18. In step 44, piezoelectric ceramic 16 is placed onto matching layer 18. In step 46, another layer of epoxy is applied to the front side of piezoelectric ceramic 16. In step 48, flexible circuit 10 is aligned so that lower pins 102 contact conductive elements 162 on piezoelectric ceramic 16. In step 50, a layer of epoxy is applied to the back side of flexible circuit 10. In step 52, backing material 12 is sandwiched with flexible circuit 10 and, finally, in step 54 pressure is applied with a press tool (not shown) to ensure there is electric contact between lower pins 102 and conductive elements 162. The pressure from the tooling and the backing material pushing onto flexible circuit 10 ensures electrical contact without using solder, and the epoxy layers cure and encompass the entire stack inside the frame to maintain the electrical contact.

As can be seen in FIG. 1, lower pins 102 extend approximately at right angles from the body of flexible circuit 10, so that once backing 12 is pressed down towards ceramic 16, lower pins 102 are in position to form the electrical contact. Positioning of lower pins 102 can also be optionally achieved with lower pins 102 extending straight out from flexible circuit 10, followed by pre-assembly bending of flexible circuit 10 around backing 12. Other variations of shaping lower pins 102 can be chosen by those skilled in the art and are all within the scope of the present disclosure.

It should be noted that the above steps of the assembling process can be combined into a lesser number of steps, broken down into more steps and/or conducted concurrently or serially in any manner, all of which are within the scope of the present disclosure.

It should also be noted that epoxy is used as an exemplary adhesive material in the above explained process. Other adhesive materials can also be considered and are within the scope of the present disclosure.

The method of solderless stack bonding of the present disclosure requires no heat and eliminates the need to solder the flexible circuit to the piezoelectric ceramic. Moreover, the heat from soldering can potentially damage the piezoelectric ceramic. The new process has reduced assembly time from 55 minutes to 25 minutes. Also it has reduced curing times from 48 hours to 2 hours.

What is claimed is:

1. A phased array ultrasonic probe comprising:
   a sheet of flexible circuit having a plurality of pins at a flexible circuit connecting edge, a backing block having a backing top and a backing bottom,
   a layer of piezoelectric ceramic forming a plurality of transducers, the transducers respectively having conductive elements formed along a ceramic connecting edge,
   a matching layer, and
   a frame,
   wherein the circuit, the backing block, the ceramic and the matching layer, with adhesive material having been applied to at least some part of each, are all aligned and stack pressed at least partially into the frame, below the backing bottom, and permanently bonded in such a fashion that each of the pins at the flexible circuit connecting edge is correspondingly, firmly and permanently in contact with a corresponding conductive element at the ceramic connecting edge.

2. The probe of claim 1, wherein the adhesive material contains at least an epoxy kind of material.

3. The probe of claim 1, wherein the backing block is in a shape of a polygonal prism in which the backing top and the backing bottom have a polygonal shape, and a cross-section of the frame in a plane parallel to the backing bottom has substantially the same polygonal shape as the shape of the backing bottom or the backing top.

4. The probe of claim 3, wherein prior to being stack pressed, a portion of the plurality of pins at the flexible circuit connecting edge extruding below the backing bottom forms lower pins, and the lower pins bend towards the backing bottom while being stack pressed.

5. The probe of claim 4, wherein the lower pins are sandwiched between the backing bottom and the ceramic after being stack pressed.

6. The probe of claim 4, wherein extremities of the lower pins form at least one line along the flexible circuit connecting edge and extremities of the conductive elements form a corresponding at least one line along the ceramic connecting edge, wherein the at least one line can be along any number of sides of the polygonal shape of the backing bottom.

7. The probe of claim 6, wherein the extremities of the lower pins end at uneven length and the extremities of the conductive elements form a correspondingly uneven front along the ceramic connecting edge, wherein the lower pins overlap correspondingly with the conductive elements sufficiently so that each of the lower pins is firmly and permanently in contact with a corresponding one of the conductive elements.

8. The probe of claim 4, wherein prior to being stack pressed, a portion of the plurality of pins at a top side opposite to the flexible circuit connecting edge extrudes above the backing top and forms upper pins, and the upper pins bend towards the backing top and are configured to be electrically coupled with an instrument intended to be coupled with the probe.

9. The probe of claim 4, wherein the flexible circuit is wrapped around the backing block on three sides, which are the backing bottom, the backing top and one side of the prism of the backing block.

10. The probe of claim 4, wherein the backing block is a right prism.

11. The probe of claim 4, wherein the flexible circuit further comprises a ground strip connecting with the plurality of pins.

12. The probe of claim 1, wherein the frame is made of rigid and electrically insulating material.

13. The probe of claim 1, wherein the frame is made of rigid plastic.

14. The probe of claim 1, wherein the frame and the block each has respective sizing and tolerance configured so that the flexible circuit, the backing block, the ceramic and the matching layer are all aligned and can be stack pressed at least partially into the frame, below the backing bottom, and permanently bonded in such a fashion that each of the pins at the flexible circuit connecting edge is correspondingly, firmly and permanently in contact with a corresponding conductive element at the ceramic connecting edge.

15. A method of making a phased array ultrasonic probe comprising the steps of:
providing a sheet of flexible circuit having a plurality of pins at a flexible circuit connecting edge,
providing a backing block having a backing top and a backing bottom,
providing a layer of piezoelectric ceramic having a plurality of conductive elements close to a second connecting edge,
providing a matching layer,
providing a frame, and,
by applying an adhesive material, and by using the frame, confining and aligning and stack pressing and permanently bonding at least partially each of the circuit, the backing block, the ceramic and the matching layer below the backing bottom so that each of the pins at the flexible circuit connecting edge is correspondingly, firmly and permanently in contact with a corresponding conductive element at the ceramic connecting edge.

16. The method of claim 15, wherein the backing block is in a shape of a polygonal prism in which the backing top and the backing bottom have a polygonal shape, and a cross-section of the frame in a plane parallel to the backing bottom has substantially the same polygonal shape as the shape of the backing bottom or the backing top.

17. The method of claim 16, wherein, prior to being stack pressed, a portion of the plurality of pins at the flexible circuit connecting edge extruding below the backing bottom forms lower pins, and the lower pins bend towards the backing bottom while being stack pressed.

18. The method of claim 16, wherein the lower pins are sandwiched between the backing bottom and the ceramic after being stack pressed.

19. The method of claim 16, wherein, prior to being stack pressed, a portion of the plurality of pins at a top side opposite to the flexible circuit connecting edge lower pins extrudes above the backing top and forms upper pins, and the upper pins bend towards the backing top and are configured to be electrically coupled with an instrument intended to be coupled with the probe.

20. The method of claim 15, wherein the adhesive material contains at least an epoxy kind of material.

\* \* \* \* \*